United States Patent
Bhirud et al.

(10) Patent No.: US 9,499,475 B2
(45) Date of Patent: Nov. 22, 2016

(54) PROCESS FOR THE PREPARATION OF ARFORMOTEROL OR SALT THEREOF

(71) Applicant: Glenmark Pharmaceuticals Limited, Mumbai (IN)

(72) Inventors: Shekhar Bhaskar Bhirud, Mumbai (IN); Suresh Mahadev Kadam, Thane (IN); Sachin Baban Gavhane, Dombivli (IN); Shailesh Shrirang Pawase, Mumbai (IN); Aniket Ashokrao Deshpande, Nashik (IN); Anil Subhash Bhujbal, Dombivli (IN)

(73) Assignee: Glenmark Pharmaceuticals Limited, Mumbai (IN)

( * ) Notice: Subject to any disclaimer, the term of this patent is extended or adjusted under 35 U.S.C. 154(b) by 0 days.

(21) Appl. No.: 14/891,014

(22) PCT Filed: May 15, 2014

(86) PCT No.: PCT/IB2014/061444
§ 371 (c)(1),
(2) Date: Nov. 13, 2015

(87) PCT Pub. No.: WO2014/184756
PCT Pub. Date: Nov. 20, 2014

(65) Prior Publication Data
US 2016/0083334 A1    Mar. 24, 2016

(30) Foreign Application Priority Data
May 17, 2013    (IN) .......................... 1762/MUM/2013

(51) Int. Cl.
*C07C 231/24*    (2006.01)
*C07C 59/255*    (2006.01)

(52) U.S. Cl.
CPC ............ *C07C 231/24* (2013.01); *C07C 59/255* (2013.01); *C07B 2200/07* (2013.01); *C07B 2200/13* (2013.01)

(58) Field of Classification Search
CPC ................. C07C 231/24; C07C 59/255; C07B 2200/07; C07B 2200/13
See application file for complete search history.

(56) References Cited

U.S. PATENT DOCUMENTS

| 6,472,563 | B1 | 10/2002 | Tanoury et al. |
| 9,309,186 | B2 * | 4/2016 | Benet-Buchholz ... C07C 231/24 |
| 2011/0014246 | A1 * | 1/2011 | Dixit ........................ A61K 9/14 424/400 |
| 2012/0053246 | A1 * | 3/2012 | Jagtap ................... A61K 31/167 514/630 |

FOREIGN PATENT DOCUMENTS

| IN | 1613/MUM/2008 | | 7/2008 |
| WO | 0021487 | A2 | 4/2000 |
| WO | 03042165 | A1 | 5/2003 |
| WO | 2009/106997 | A2 | 9/2009 |
| WO | 2013/136061 | * | 9/2013 |

* cited by examiner

*Primary Examiner* — Shailendra Kumar
(74) *Attorney, Agent, or Firm* — M. Carmen & Associates, PLLC

(57) ABSTRACT

Provided is an improved process for the preparation of arformoterol L-(+)-tartrate, and more specifically provided is a novel process for the preparation of arformoterol L-(+)-tartrate via arformoterol D-(−)-tartrate.

11 Claims, 3 Drawing Sheets

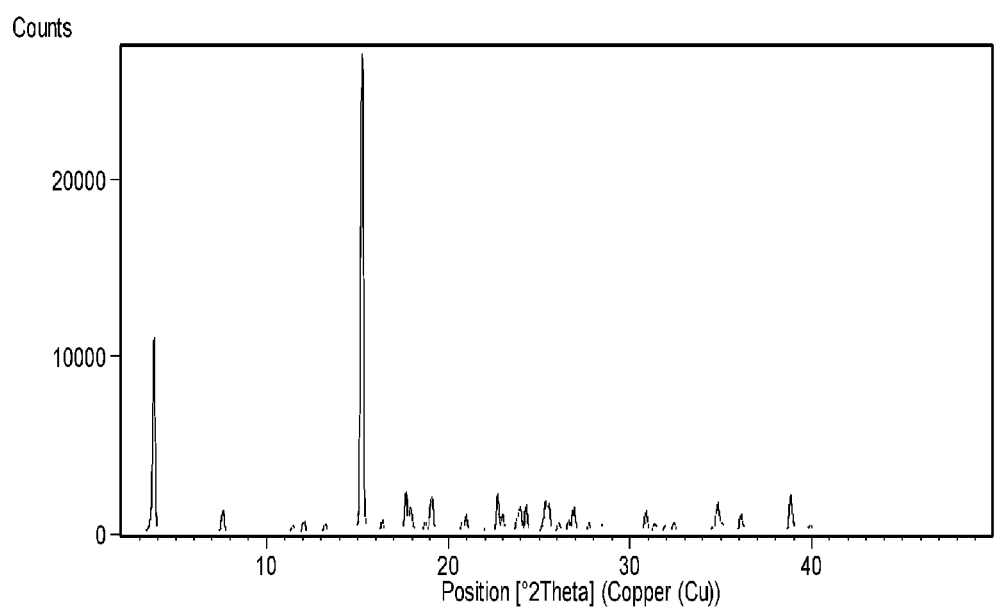
Figure 1: is an X-ray powder diffraction pattern of arformoterol D-(-)-tartrate compound of formula II according to example 4.

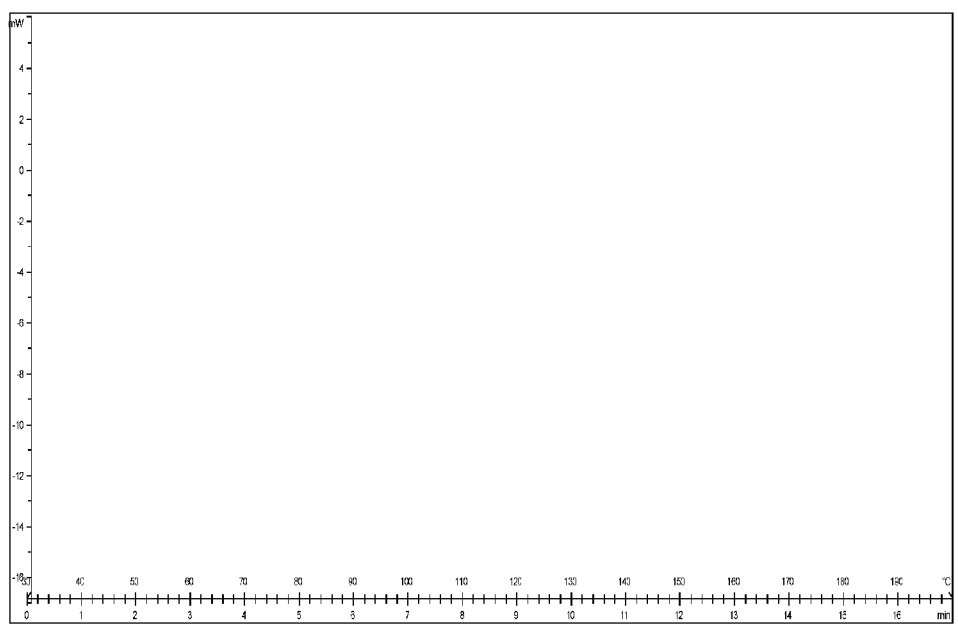
Figure 2: is DSC pattern of arformoterol D-(-)-tartrate compound of formula II according to example 4

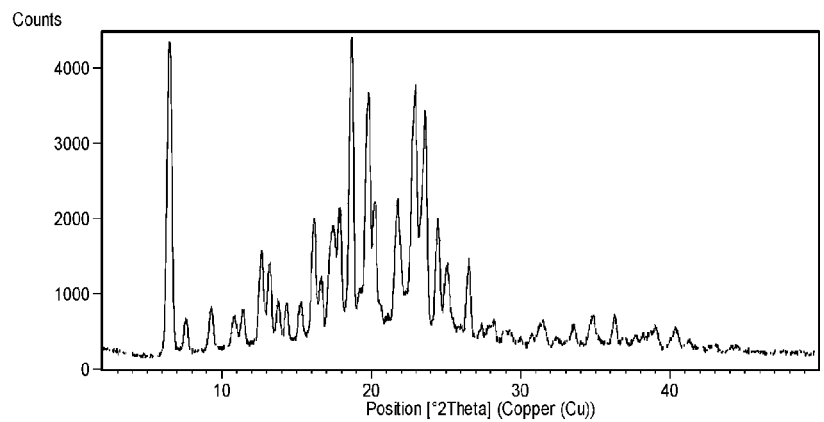
Figure 3: X-ray powder diffraction pattern of arformoterol L(+) tartrate compound of formula Ia according to example 6.
Glenmark Generics Limited
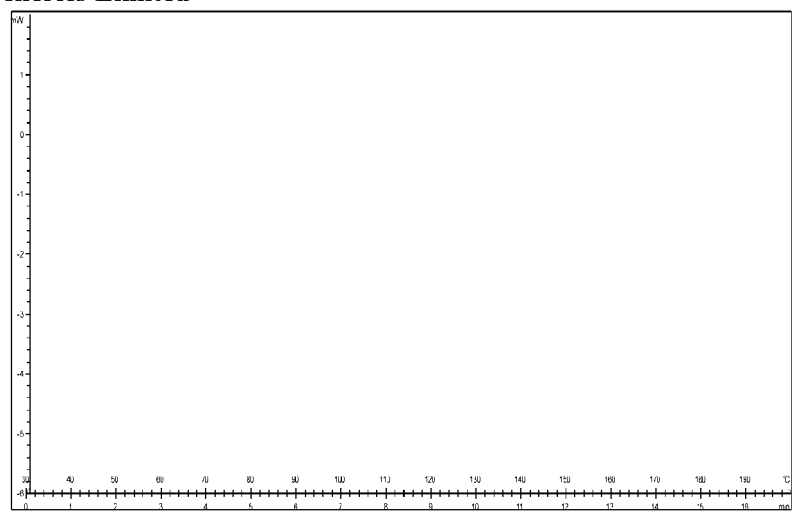
Figure 4: DSC of arformoterol L(+) tartrate compound of formula Ia according to example 6

PROCESS FOR THE PREPARATION OF ARFORMOTEROL OR SALT THEREOF

PRIORITY

This application claims priority under 35 U.S.C. §371 to International Application No. PCT/IB2014/061444, filed May 15, 2014 which claims the benefit of Indian Provisional Application No. 1762/MUM/2013, filed May 17, 2013, the contents of which are incorporated by reference herein.

FIELD OF THE INVENTION

The present invention relates to an improved process for the preparation of arformoterol L-(+)-tartrate. More specifically the present invention relates to a novel process for the preparation of arformoterol L-(+)-tartrate via arformoterol D-(−)-tartrate.

BACKGROUND OF THE INVENTION

Arformoterol tartrate is the United States Adopted Name (USAN) for (R,R) formoterol L-tartrate. The chemical name for arformoterol tartrate is formamide, N-[2-hydroxy-5-[(1R)-1-hydroxy-2-[[(1R)-2(4-methoxyphenyl)-1-methylethyl]amino]ethyl]phenyl]-, (2R,3R)-2,3dihydroxybutanedioate (1:1 salt), and is represented by formula (Ia):

Formula Ia

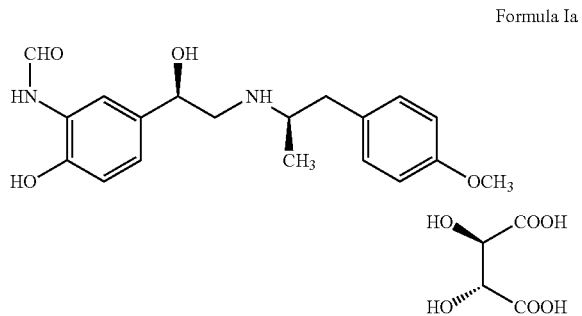

Arformoterol tartrate is currently marketed in the United States under the trade name BROVANA®. BROVANA® (arformoterol tartrate) Inhalation Solution is supplied as 2 mL of arformoterol tartrate solution packaged in 2.1 mL unit-dose, low-density polyethylene (LDPE) unit-dose vials. Each unit-dose vial contains 15 mcg of arformoterol (equivalent to 22 mcg of arformoterol tartrate) in a sterile, isotonic saline solution, pH-adjusted to 5.0 with citric acid and sodium citrate.

U.S. Pat. No. 6,472,563 discloses polymorphic Form A, B and C of arformoterol L-(+)-tartrate. The specification recites that the product described in the art, U.S. Pat. No. 6,268,533 as it initially crystallizes, contains four identified chemical impurities and no matter how many times the product is recrystallized the resultant polymorph A contains at least 0.5% of impurities. Further the specification of US'563 discloses that conditions of recrystallization may result in partial hydrolysis and lead to the formation of impurities and that it may be possible that some degradation occurs and impurities are introduced in the recrystallization process.

For the development of an active pharmaceutical ingredient two factors are important namely the impurity profile of the active pharmaceutical ingredient and the polymorphic Form that is to be targeted. The known art discloses that crystallization conditions and method of isolation of Arformoterol L-(+)-tartrate may lead to varied polymorphic Forms A, B, C or mixtures thereof with different levels of impurities, compounds of Formula A, B, C and/or D.

Formula A

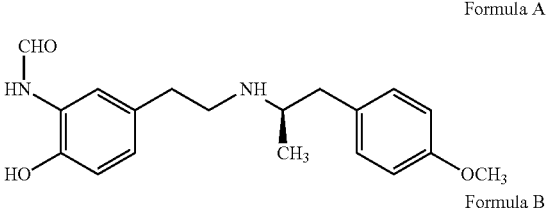

Formula B

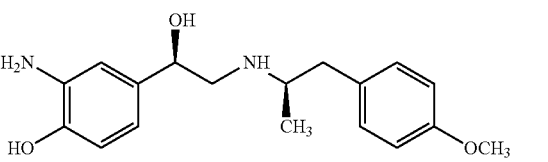

Formula C

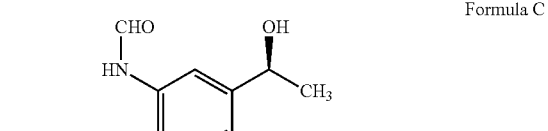

Formula D

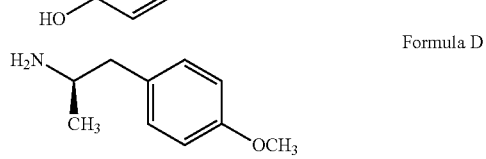

The art discloses that polymorphic Form B of Arformoterol L-(+)-tartrate can be obtained in a crude state only and attempts to improve the chemical purity of Form B by altering the temperature and ratios of solvents leads to interconversion to polymorphic Form C. The temperature and the ratios of solvents used are not only critical for removal of chemical impurities but important for crystal morphology also. Thus when optimization of chemical purity of Arformoterol L-(+)-tartrate occurs, the polymorphic Form B does not remain same and is converted to Form C. Thus the state of art does not disclose a process for the preparation of Arformoterol L-(+)-tartrate in polymorphic Form B and substantially free of impurities, compounds of Formula A, B, C, D and/or E.

Formula E

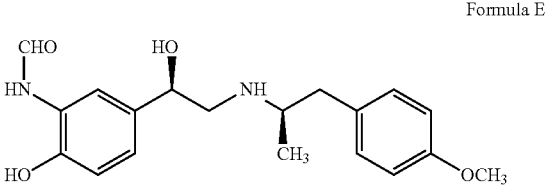 [SMILES: COc1ccc(C[C@@H](C)NC[C@H](O)c2ccc(O)c(NC=O)c2)cc1]

The process of conversion of crude arformoterol to arformoterol L-(+)-tartrate, in the art entails use of specific solvent systems to meet the desired standards of chemical, chiral and polymorphic Form purity but is still unable to obtain polymorphic Form B in desired chemical purity and uncontaminated with other polymorphic Forms.

We have also found that when crude arformoterol base is subjected to reaction with L (+) tartaric acid in a solvent, the arformoterol L-(+)-tartrate cannot be obtained in desired polymorphic Form B and chemical purity and is contaminated with other polymorphic forms. Further, when crude arformoterol base with impurities, compounds of Formula A, B, C, D and/or E is subjected to reaction with L (+) tartaric acid in aqueous tetrahydrofuran system, to improve the chemical and chiral purity, the arformoterol L-(+)-tartrate cannot be obtained in desired chemical purity and polymorphic Form B and is usually contaminated with other polymorphic forms.

Therefore, there is a need for an improved process for the preparation of arformoterol L-(+)-tartrate in desired single polymorphic Form B, uncontaminated with other polymorphic Forms A and C and substantially free of impurities, compounds of Formula A, B, C, D and/or E. The need in the art is to provide a reliable and reproducible process to prepare consistently the desired polymorphic Form B of arformoterol L-(+)-tartrate having a chemical purity of at least 99% and a chiral purity of at least 99% without using chromatographic purification techniques.

The present invention provides a process which is simple, ecofriendly, inexpensive, reproducible, robust and well suited on commercial scale and circumvents the likely formation of isomeric and other process-related impurities; while ensuring a target polymorphic form of arformoterol tartrate product with optimum yield and polymorphic and chemical purity.

In the process of the present invention, the crude arformoterol is reacted with D-(−)-tartaric acid to form arformoterol D-(−)-tartrate, which is then reacted with a base and L-(+)-tartaric acid to provide high purity arformoterol L-(+)-tartrate. Surprisingly, we have found that the present process via arformoterol D-(−)-tartrate affords high purity arformoterol L-(+)-tartrate, substantially free of impurities, compounds of Formula A, B, C, D and/or E and in desired polymorphic Form B, in contrast to the known method of conversion of crude arformoterol to arformoterol L-(+)-tartrate by reacting it with L-(+)-tartaric acid.

BRIEF DESCRIPTION OF THE ACCOMPANYING FIGURES

FIG. 1: PXRD pattern of arformoterol D-(−)-tartrate, compound of formula II, according to example 4.

FIG. 2: Differential scanning calorimetry endotherm of arformoterol D-(−)-tartrate, compound of formula II according to example 4.

FIG. 3: PXRD pattern of arformoterol L-(+)-tartrate, compound of formula Ia, according to example 6.

FIG. 4: Differential scanning calorimetry endotherm of arformoterol L-(+)-tartrate, compound of formula Ia, according to example 6.

SUMMARY OF INVENTION

The present invention provides a process for the preparation of arformoterol L-(+)-tartrate, a compound of Formula Ia,

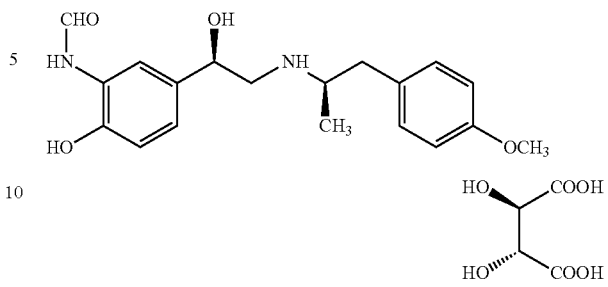

Formula Ia wherein the level of compounds of formula A or B, is less than 0.15% w/w relative to the amount of arformoterol L-(+)-tartrate as determined by HPLC,

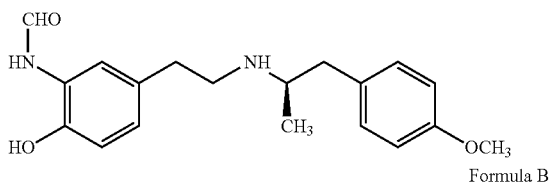

Formula A

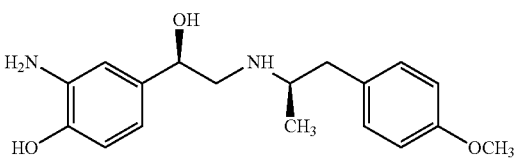

Formula B comprising: a) reacting crude arformoterol, a compound of Formula I

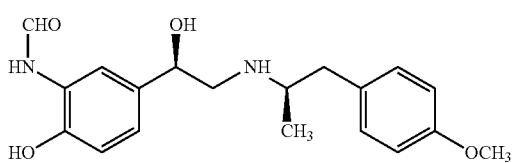

Formula I with D-(−)-tartaric acid to form arformoterol D-(−)-tartrate, a compound of formula II; and

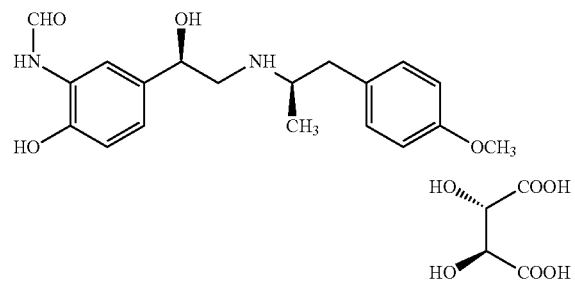

Formula II b) reacting the arformoterol D-(−)-tartrate, the compound of formula II, with a base and L-(+)-tartaric acid, to form arformoterol L-(+)-tartrate, compound of Formula Ia.

DETAILED DESCRIPTION OF INVENTION

The present invention provides a process for the preparation of arformoterol L-(+)-tartrate, a compound of Formula Ia, Formula Ia

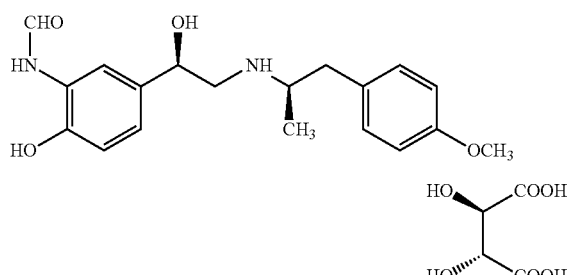

substantially free of one or more of the compounds of formula A, B, C, D or E and their salt thereof as determined by HPLC Formula A

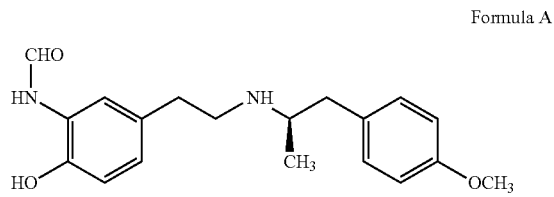

Formula B

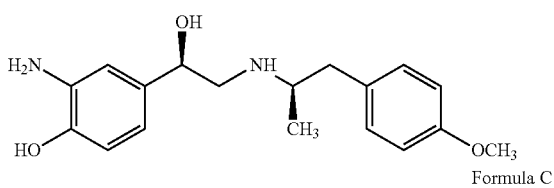

Formula C

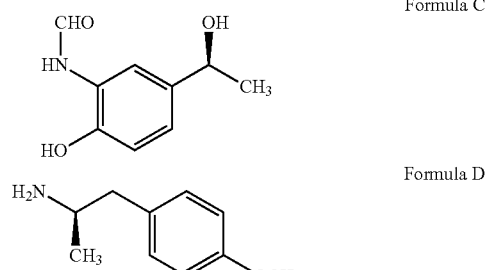

Formula D

Formula E

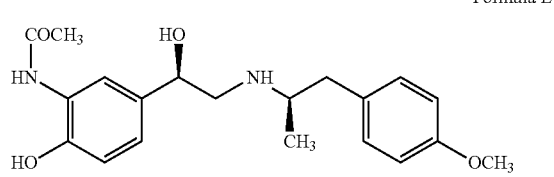

comprising: a) reacting crude arformoterol, a compound of Formula I

Formula I

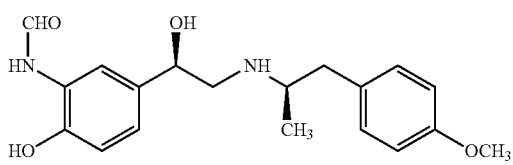

with D-(−)-tartaric acid to form arformoterol D-(−)-tartrate, a compound of formula II; and Formula II

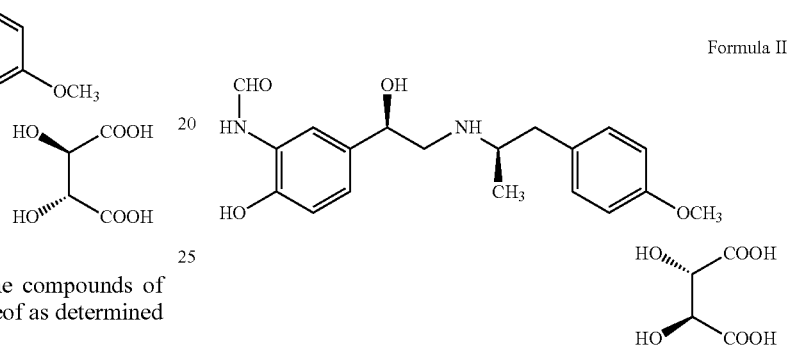

b) reacting the arformoterol D-(−)-tartrate, the compound of formula II, with a base and L-(+)-tartaric acid, to form arformoterol L-(+)-tartrate, compound of Formula Ia.

By "substantially free of one or more of the compounds of formula A, B, C, D or E" is meant that the arformoterol L-(+)-tartrate, a compound of Formula Ia prepared in accordance with the present invention contains less than about 0.5% w/w, more preferably less than about 0.1% w/w, and even more preferably, less than about 0.05% w/w of one or more of the compounds of formula A, B, C, D and E, relative to the amount of arformoterol L-(+)-tartrate as confirmed by HPLC.

The present invention provides a process for the preparation of arformoterol L-(+)-tartrate, a compound of Formula Ia, Formula Ia

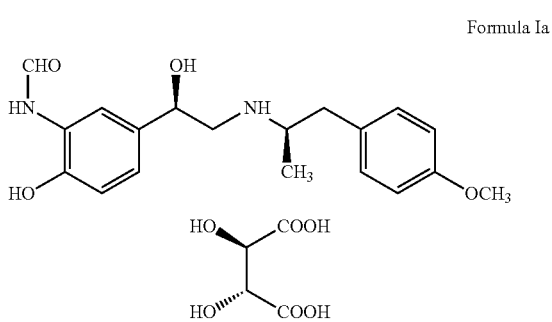

wherein the level of compounds of formula A, B, C, D or E is less than 0.15% w/w relative to the amount of arformoterol L-(+)-tartrate as determined by HPLC a) reacting crude arformoterol, a compound of Formula I

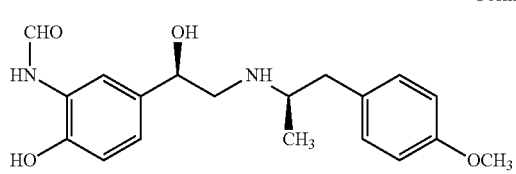
Formula I with D-(−)-tartaric acid to form arformoterol D-(−)-tartrate, a compound of formula II; and

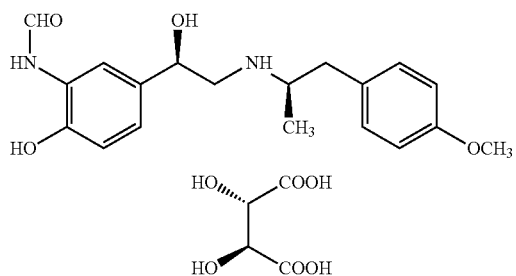
Formula II b) reacting the arformoterol D-(−)-tartrate, the compound of formula II, with a base and L-(+)-tartaric acid, to form arformoterol L-(+)-tartrate, compound of Formula Ia.

The present invention provides a process for the preparation of arformoterol L-(+)-tartrate, a compound of Formula Ia,

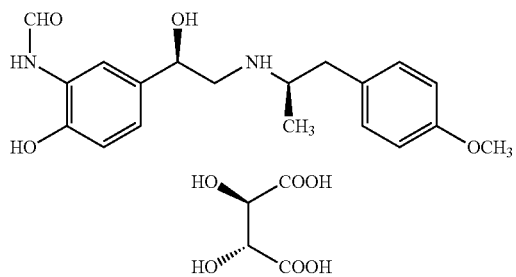
Formula Ia wherein the level of compounds of formula A or B, is less than 0.15% w/w relative to the amount of arformoterol L-(+)-tartrate as determined by HPLC

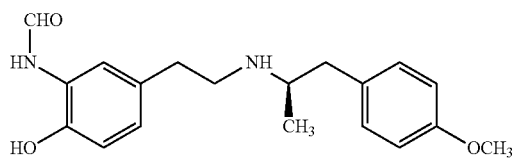
Formula A

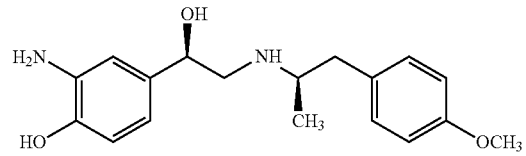
Formula B comprising: a) reacting crude arformoterol, a compound of Formula I

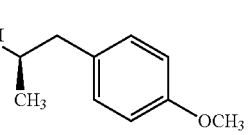
Formula I with D-(−)-tartaric acid to form arformoterol D-(−)-tartrate, a compound of formula II; and

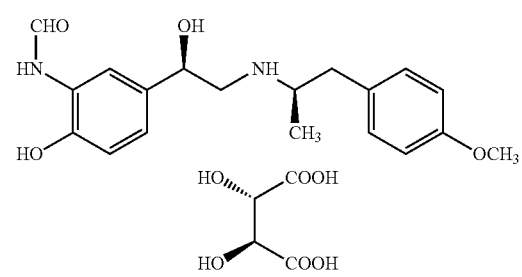
Formula II b) reacting the arformoterol D-(−)-tartrate, the compound of formula II, with a base and L-(+)-tartaric acid, to form arformoterol L-(+)-tartrate, compound of Formula Ia.

In one embodiment, of the process of the present invention, the crude arformoterol, compound of formula I is obtained by a process comprising hydrogenating a compound of formula III in a solvent system.

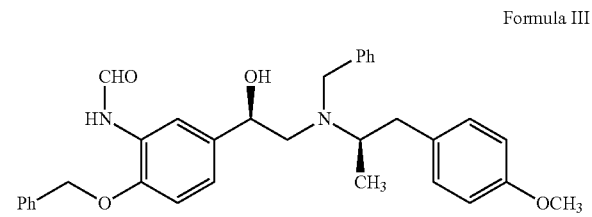 [SMILES: COc1ccc(C[C@@H](C)N(Cc2ccccc2)C[C@H](O)c2ccc(OCc3ccccc3)c(NC=O)c2)cc1]
Formula III

The hydrogenation of compound of formula III may be carried out using metal catalysts such as platinum, palladium, nickel, rhodium or ruthenium supported on solid supports like calcium carbonate, alumina, barium sulfate, silica or activated charcoal carbon.

The hydrogenation of compound of formula III may be carried out in the presence of hydrogen or hydrogen transfer reagents selected from formic acid, salts of formic acid, phosphonic acid, hydrazine, where hydrogen is preferred.

The hydrogenation of compound of formula III may be carried out in a solvent system selected from alcohols, esters and the like.

The alcohols may be selected from the group consisting of methanol, ethanol, propanol, isopropanol, n-butanol, sec. butanol and the like.

The esters solvent may be selected from the group consisting of ethyl acetate, isopropyl acetate, isobutyl acetate, t-butyl acetate and the like.

In one embodiment, the crude arformoterol is obtained by hydrogenation of compound of formula III, and subjecting the reaction mass to filtration to remove the catalyst to obtain the crude arformoterol in the filtrate.

In one embodiment, the crude arformoterol present in the filtrate may be used for further reaction with D-(−)-tartaric acid, without isolating it from the filtrate.

In one embodiment, the crude arformoterol present in the filtrate may be isolated in a solid form or as a residue by removal of the solvent by evaporation or distillation. The isolated solid crude arformoterol may be then subjected to reaction with D-(−)-tartaric acid In one embodiment, of the process of the present invention the crude arformoterol was obtained by a process comprising hydrogenating the compound of formula III with Pd/C in a solvent system followed by filtration.

In one embodiment the "crude arformoterol" means arformoterol having a chemical purity of 50-99.5% as determined by HPLC.

The reaction of crude arformoterol with D-(−)-tartaric acid to form arformoterol D-(−)-tartrate, a compound of formula II, may be carried out in a solvent system selected from the group consisting of alcohols, hydrocarbons, halogenated hydrocarbons, ethers, esters, water or mixtures thereof.

The alcohols may be selected from the group consisting of methanol, ethanol, propanol, isopropanol, n-butanol, sec. butanol and the like.

The hydrocarbons may be selected from the group consisting of pentane, n-hexane, heptane, cyclohexane, petroleum ether, benzene, toluene, m-, o-, or p-xylene and the like.

The halogenated hydrocarbons may be selected from the group consisting of dichloromethane (MDC), 1,2-dichloroethane and the like.

The ethers may be selected from the group consisting of diethyl ether, di-isopropyl ether, tetrahydrofuran, 1,4-dioxane, tetrahydropyran and the like.

The esters solvent may be selected from the group consisting of ethyl acetate, isopropyl acetate, isobutyl acetate, t-butyl acetate and the like.

The D-(−)-tartaric acid may be added directly to crude arformoterol in a solvent system or an aqueous solution of D-(−)-tartaric acid may be added to crude arformoterol in a solvent system.

In one embodiment, a solution of D-(−)-tartaric acid in water is added to crude arformoterol present in a mixture of alcohol and hydrocarbon solvent system. Preferably isopropyl alcohol and toluene mixture.

In one embodiment, the reaction of crude arformoterol with D-(−)-tartaric acid to form arformoterol D-(−)-tartrate is carried out in isopropanol and toluene system to obtain arformoterol D-(−)-tartrate.

In one embodiment, a solution of D-(−)-tartaric acid in water is added to crude arformoterol present in a mixture of ethanol and isopropanol solvent system to obtain arformoterol D-(−)-tartrate.

In one embodiment, the reaction of crude arformoterol with D-(−)-tartaric acid to form arformoterol D-(−)-tartrate is carried out in ethanol-isopropanol (70:30) system to obtain arformoterol D-(−)-tartrate.

In one embodiment, the arformoterol D-(−)-tartrate, compound of formula II, is subjected to purification, prior to reacting with L-(+)-tartaric acid.

The purification may be carried out by crystallization of arformoterol D-(−)-tartrate, compound of formula II in a solvent system comprising ether, alcohol, ketone, hydrocarbon, halogenated hydrocarbon, water or mixture thereof.

The ether solvent may be selected from the group consisting of tetrahydrofuran, tetrahydropyran, 1,4 dioxane and the like. Preferably tetrahydrofuran.

The alcohol solvent may be selected from the group consisting of methanol, ethanol, propanol, isopropanol, isobutanol, 2-butanol and the like.

The ketone solvent may be selected from the group consisting of acetone, methyl ethyl ketone, ethyl methyl ketone and the like.

The hydrocarbon solvent may be selected from the group consisting of n-pentane, n-hexane, heptane, cyclohexane, petroleum ether, benzene, toluene, m-, o-, or p-xylene and the like.

The halogenated hydrocarbon solvent may be selected from the group consisting of dichloromethane (MDC), 1,2-dichloroethane and the like.

In one embodiment, the arformoterol D-tartrate compound of formula II is subjected to purification by crystallization in a solvent system comprising ether and water.

In one embodiment, the present invention provides a process for preparation of arformoterol D-(−)-tartrate having a chemical purity of at least 95% as determined by HPLC comprising subjecting the arformoterol D-(−)-tartrate a compound of formula II to purification by crystallization with tetrahydrofuran and water.

In one embodiment, the present invention provides a process for the preparation of arformoterol D-(−)-tartrate in a chemical purity of at least 95% as determined by HPLC by a process comprising:
a) adding tetrahydrofuran to arformoterol D-(−)-tartrate to form a mixture;
b) refluxing the mixture;
c) adding water to the refluxing mixture to form a clear solution;
d) adding tetrahydrofuran to the clear solution; and
e) cooling the solution of step (d) to obtain arformoterol D-(−)-tartrate in a chemical purity of at least 95% as determined by HPLC In one embodiment in step a) tetrahydrofuran was added to arformoterol D-(−)-tartrate at room temperature.

In step b) the mixture of arformoterol D-(−)-tartrate and tetrahydrofuran was refluxed at about 60-80° C.;

In step c) water was added slowly at the temperature in the range of about 60-80° C. followed by stirring for a period of 10-40 minutes to form a clear homogeneous solution.

In step d) tetrahydrofuran was added slowly to the clear homogeneous solution in step c; at the temperature in the range of about 60-80° C.; and In step e) the clear solution of step d was cooled with stirring to room temperature for a period of about 3-8 hours.

The purification process of arformoterol D-(−)-tartrate may be carried out once or repeatedly to increase the chemical and chiral purity of arformoterol D-(−)-tartrate to the desired level.

In one embodiment, the present invention provides arformoterol D-(−)-tartrate in a chemical purity of at least 99% and chiral purity of least 99% as determined by HPLC after repeatedly purifying it by purification as described above.

The crude arformoterol D-(−)-tartrate obtained when subjected to purification by recrystallization from aqueous tetrahydrofuran system, results in arformoterol D-(−)-tartrate of chemical purity of at least 99% and a chiral purity of at least 99% as determined by HPLC. The conversion of highly pure arformoterol D-(−)-tartrate with L-(+)-tartaric acid in presence of a base results in arformoterol L-(+)-tartrate in single polymorphic Form, more specifically Form B with a high degree of chemical and chiral purity.

In step b, the conversion of arformoterol D-(−)-tartrate, to arformoterol L-(+)-tartrate is carried out with a base and L-(+)-tartaric acid.

The base may be selected from an inorganic base or an organic base.

The inorganic base may be selected from the group consisting of alkali metal hydroxides such as sodium hydroxide, potassium hydroxide, barium hydroxide, lithium hydroxide and the like; metal carbonates such as sodium carbonate, potassium carbonate, magnesium carbonate, and calcium carbonate and the like; metal bicarbonates such as sodium bicarbonate, potassium bicarbonate and the like; alkoxides such as sodium methoxide, potassium methoxide, sodium tert-butoxide, potassium tert-butoxide and the like or aqueous mixture thereof. Preferably, sodium bicarbonate.

The organic base may be selected from triethyl amine, trimethyl amine, diisopropyl ethylamine, dimethyl amino pyridine, picoline, dimethyl amino pyridine and pyridine.

In one embodiment the conversion of arformoterol D-(−)-tartrate, to arformoterol L-(+)-tartrate is carried out with a base and L-(+)-tartaric acid and a solvent.

The solvent may be selected from the group consisting of ester, hydrocarbon, halogenated hydrocarbon, water or mixture thereof.

The esters solvent may be selected from the group consisting of methyl acetate, ethyl acetate, isopropyl acetate, isobutyl acetate, t-butyl acetate and the like. Preferably, ethyl acetate.

The hydrocarbon solvent may be selected from the group consisting of n-pentane, n-hexane, heptane, cyclohexane, petroleum ether, benzene, toluene, m-, o-, or p-xylene and the like.

The halogenated hydrocarbon solvent may be selected from the group consisting of dichloromethane (MDC), 1,2-dichloroethane and the like.

In one embodiment, in step b) the arformoterol D-(−)-tartrate, base and L-(+)-tartaric acid are added simultaneously.

In one embodiment, in step b) the arformoterol D-(−)-tartrate, the compound of formula II is reacted with a base to obtain arformoterol, followed by reacting the arformoterol with L-(+)-tartaric acid to form arformoterol L-(+)-tartrate.

The reaction of arformoterol D-(−)-tartrate, the compound of formula II with a base produces arformoterol, compound of Formula I which can be isolated from the reaction mixture before reacting it with L-(+)-tartaric acid. Alternatively the L-(+)-tartaric acid is added to the reaction mass containing arformoterol in-situ to obtain arformoterol L-(+)-tartrate.

In one embodiment, the arformoterol D-(−)-tartrate, the compound of formula II is reacted with a base to produce arformoterol, the compound of formula I, which is not isolated from the reaction mixture and is reacted in-situ with L-(+)-tartaric acid.

In one embodiment, the arformoterol D-(−)-tartrate, the compound of formula II is reacted with a base to produce arformoterol, which is isolated as a residue or solid. The isolated solid or residue of arformoterol thus obtained is then reacted with L-(+)-tartaric acid.

In one embodiment, the conversion of arformoterol D-(−)-tartrate, to arformoterol L-(+)-tartrate is carried out by reacting arformoterol D-(−)-tartrate with a base to obtain arformoterol which is isolated from the reaction mixture as a residue and treated with L-(+)-tartaric acid to obtain arformoterol L-(+)-tartrate, a compound of Formula Ia.

In one embodiment, the present invention provides a process for preparation of arformoterol L-(+)-tartrate, a compound of Formula Ia, comprising reacting the arformoterol D-(−)-tartrate, the compound of formula II with a base and L-(+)-tartaric acid.

In one embodiment, in step b) the arformoterol D-(−)-tartrate, the compound of formula II is reacted with a base to obtain arformoterol, followed by reacting the arformoterol with L-(+)-tartaric acid in a mixture of toluene and isopropanol to form arformoterol L-(+)-tartrate In one embodiment, the isopropanol and toluene are used in the ratio of 8:2 v/v.

In one embodiment, an aqueous solution of L-(+)-tartaric acid is used.

In one embodiment, the aqueous solution of L-(+)-tartaric acid is used in a proportion such that isopropanol:toluene:water is in the ratio of 8:2:1 v/v, for 1 part by weight of arformoterol D-(−)-tartrate.

In one embodiment, the present invention provides a process for preparation of arformoterol L-(+)-tartrate, a compound of Formula Ia, in polymorphic Form B, comprising reacting the arformoterol D-(−)-tartrate, the compound of formula II with a base and L-(+)-tartaric acid, in a mixture of toluene and isopropanol.

In one embodiment, the present invention provides a process for preparation of arformoterol L-(+)-tartrate, a compound of Formula Ia, characterized by X-ray diffraction (XRD) spectrum having peak reflections at about 8.69, 17.44, 20.63, 21.96, 22.74±0.2 degrees 2 theta, comprising reacting the arformoterol D-(−)-tartrate, the compound of formula II with a base and L-(+)-tartaric acid, in a mixture of toluene and isopropanol.

In one embodiment, the present invention provides a process for preparation of arformoterol L-(+)-tartrate, a compound of Formula Ia, in polymorphic Form B, wherein the aqueous solution of L-(+)-tartaric acid is used in a proportion such that isopropanol:toluene:water is in the ratio of 8:2:1 v/v, for 1 part by weight of arformoterol D-(−)-tartrate.

Advantageously in one embodiment, the implementation of the process of the present invention provides polymorphic Form B, of arformoterol L-(+)-tartrate, a compound of Formula Ia, reproducibly without contamination of polymorphic Form C and polymorphic Form A and in desired chemical and chiral purity. The arformoterol L-(+)-tartrate, obtained by the process of the present invention has a chemical purity of at least 99% and a chiral purity of at least 99% without using chromatographic purification techniques.

Purification of arformoterol L-(+)-tartrate, Form B by methods known in the art where crude arformoterol L-(+)-tartrate, Form B slurry obtained was heated at 45-50° C. for removal of impurities leads to Form C of arformoterol L-(+)-tartrate which on further crystallization from aqueous isopropyl alcohol leads to Form A. The process of the present invention provides for isolation of Form B without isolation or formation of Form A and Form C during the overall purification process.

The present invention provides use of arformoterol D-(−)-tartrate, compound of formula II, in the process for preparation of arformoterol L-(+)-tartrate, compound of Formula Ia.

The present invention provides use of arformoterol D-(−)-tartrate, compound of formula II, in the process for preparation of arformoterol L-(+)-tartrate, compound of Formula Ia in crystalline polymorphic Form B.

The present invention provides use of arformoterol D-(−)-tartrate, compound of formula II, in the process for preparation of arformoterol L-(+)-tartrate, compound of Formula Ia in crystalline polymorphic Form B, wherein the level of compounds of formula A or B, is less than 0.15% w/w relative to the amount of arformoterol L-(+)-tartrate as determined by HPLC.

In one embodiment, the present invention provides arformoterol D-(−)-tartrate, compound of formula II characterized by X-ray diffraction (XRD) spectrum having peak reflections at about 3.82, 15.44 and 17.79±0.2 degrees 2 theta.

In one embodiment, the present invention provides arformoterol L-(+)-tartrate, a compound of Formula Ia, wherein the level of compounds of formula A or B, is less than 0.15% w/w relative to the amount of arformoterol L-(+)-tartrate as determined by HPLC in crystalline polymorphic Form B.

In one embodiment, the present invention provides arformoterol L-(+)-tartrate, a compound of Formula Ia, wherein the level of compounds of formula A or B, is less than 0.15% w/w relative to the amount of arformoterol L-(+)-tartrate as determined by HPLC in crystalline polymorphic Form B and a chiral purity of at least 99%.

In one embodiment, the present invention provides arformoterol L-(+)-tartrate, a compound of Formula Ia, wherein the level of compounds of formula A or B, is less than 0.15% w/w relative to the amount of arformoterol L-(+)-tartrate as determined by HPLC in crystalline polymorphic Form B and wherein the level of polymorphic Form A and/or C is less than 1%.

In one embodiment, the present invention provides a process for preparation of arformoterol having chemical purity of at least 99% as determined by HPLC, comprising reacting arformoterol D-(−)-tartrate with a base. The base may be selected as described supra.

In one embodiment, the present invention provides a process for the preparation of a compound of Formula III, comprising: reacting a compound of Formula IV, with a compound of Formula V Formula IV

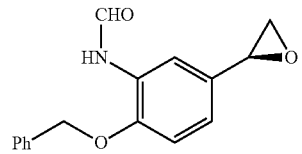

Formula V

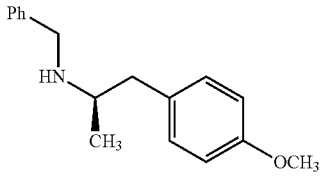

to form a compound of Formula III,

Formula III

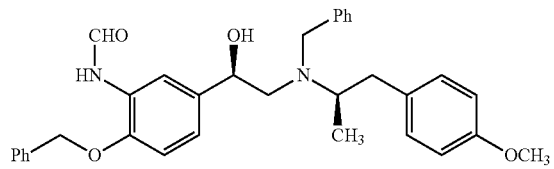

In one embodiment the present invention provides a process for the preparation of arformoterol L-(+)-tartrate, a compound of Formula Ia, Formula Ia

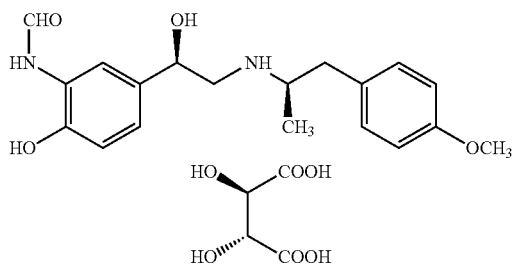

substantially free of one or more of the compounds of formula A, B, C, D and E as determined by HPLC Formula A

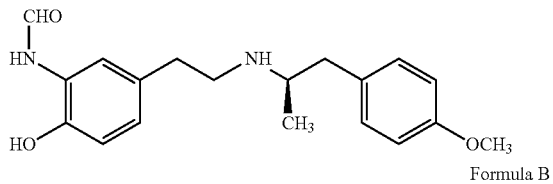

Formula B

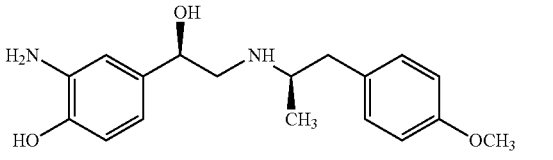

Formula C

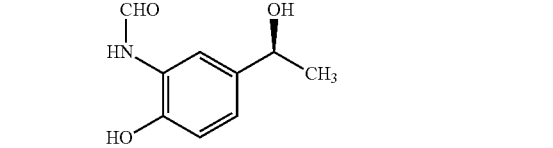

Formula D

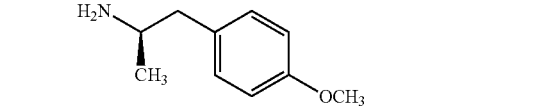

Formula E

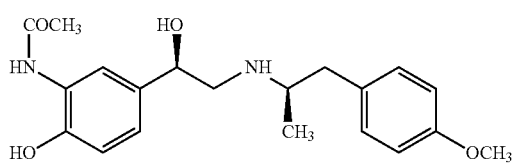

comprising:
(a) adding tetrahydrofuran to arformoterol L-(+)-tartrate to form a mixture;
(b) refluxing the mixture;
(c) adding water to the refluxing mixture to form a clear solution;
(d) adding tetrahydrofuran to the clear solution; and
(e) cooling the solution of step (d) to obtain arformoterol L-(+)-tartrate in a chemical purity of at least 95% as determined by HPLC In one embodiment the present invention provides novel polymorphic form of arformoterol L-(+)-tartrate characterized by X-ray Diffraction (XRD) spectrum having peak reflections at about 6.63, 16.20, 18.74, 19.86, 22.97, 23.64±0.2 degrees 2 theta.

In one embodiment the present invention provides novel polymorphic form of arformoterol L-(+)-tartrate characterized by Differential Scanning calorimetric (DSC) thermogram having an endotherm at about 128.4°±1° C., 174.82±1° C., 180.26±1° C. and exotherm at about 137.21±1° C.

In one embodiment, the present invention provides arformoterol L-(+)-tartrate, a compound of formula Ia, obtained by the processes herein described, having a $D_{90}$ particle size of about 35 microns, $D_{50}$ particle size of about 16 microns and $D_{10}$ particle size of about 6 microns.

In one embodiment, the present invention provides micronized arformoterol L-(+)-tartrate, a compound of formula Ia, obtained by the processes herein described, having a $D_{90}$ particle size of about 7 microns, $D_{50}$ particle size of about 4 microns and $D_{10}$ particle size of about 2 microns.

In one embodiment the present invention provides arformoterol L-(+)-tartrate, a compound of formula Ia, having bulk density of 0.159 g/cc.

In one embodiment the present invention provides arformoterol L-(+)-tartrate, a compound of formula Ia, having taped density of 0.271 g/cc.

In one embodiment the present invention provides arformoterol L-(+)-tartrate, a compound of formula Ia, having specific surface area of about 8.44 m²/g.

In one embodiment the present invention provides arformoterol L-(+)-tartrate, a compound of formula Ia, having Hausner ratio of 1.70.

In one embodiment the present invention provides arformoterol L-(+)-tartrate, a compound of formula Ia, having aspect ratio of 1.12 to 2.47

Instrumental Settings for XRPD:

The measurements were performed on Philips X-Ray Diffractometer model XPERT-PRO (PANalytical) Detector: X'celerator [1] using Cu lamp with type and wavelength of the X-ray radiation: K-$\alpha_1$ 1.54060 [Å], K-$\alpha_2$ 1.5444 [Å].

Instrumental Settings for DSC:

The DSC thermogram was measured by a Differential Scanning calorimeter (DSC 822, Mettler Toledo) at a scan rate of 10° C. per minute in the temperature range of range is "25° C. to 350° C.". The DSC module was calibrated with Indium and zinc standard.

Related Substances by HPLC:

Reagents and Solvents:

Water (Milli Q or equivalent); Acetonitrile (HPLC grade); Sodium dihydrogen phosphate (AR grade) Di-sodium hydrogen phosphate (AR grade); Potassium dihydrogen phosphate (AR grade) Ortho phosphoric acid (AR grade)

Chromatographic Conditions:

Apparatus:

A High Performance Liquid Chromatograph equipped with quaternary gradient pumps, variable wavelength UV detector attached with data recorder and Integrator software or equivalent.

Column:

Inertsil C8, 250' 4.6 mm, 5.0 m or equivalent; Mobile phase: A=Buffer, B=Acetonitrile (Gradient Program)

Buffer:

3.75 gm of Sodium dihydrogen phosphate in 1000 mL water, pH adjusted to 3.0 with dilute ortho phosphoric acid solution. Filter through 0.45µ filter paper and degas. Diluent: Solution A: Acetonitrile (84:16 v/v)

Solution A:

6.1 g Potassium dihydrogen phosphate+1.03 g Di-sodium hydrogen phosphate to 1000 mL, pH adjusted to 6.0 with dilute ortho phosphoric acid solution. Filter through 0.45µ filter paper and degas.

Flow Rate:

1.0 mL/minute; Detection wavelength: UV 214 nm Column temperature: 25° C. Injection volume: 20 mL; Run time: 55 minutes Gradient Program:

| Time (minute) | A (%) | B (%) |
| --- | --- | --- |
| 0.01 | 84 | 16 |
| 10 | 84 | 16 |
| 37 | 30 | 70 |
| 40 | 84 | 16 |
| 55 | 84 | 16 |

Preparation of Reference Solution:

Weigh accurately about 25 mg of Arformoterol tartrate reference standard and transfer it into a 50 mL volumetric flask. Add 30 mL of diluent and sonicate to dissolve. Make up to the mark with diluent & mix. Further dilute 1 mL to 200 mL with diluent.

Preparation of Test Solution: (Prepare in Duplicate)

Weigh accurately about 25 mg of test sample and transfer it into a 50 mL volumetric flask. Add 30 mL of diluent and sonicate to dissolve. Make up to the mark with diluent & mix.

Procedure:

Inject the blank, six replicate injections of reference solution and then inject each of test solution. Record the chromatograms for all injections.

System Suitability:

The relative standard deviation (RSD) for peak area responses and retention time of six replicate injections of reference solution should not be more than 5.0%. It is observed that Arformoterol tartrate is eluted at retention time of about 16 minutes.

$$\% \text{ Individual Impurity} = \frac{\text{Area of Individual Impurity in test solution}}{\text{Average area of Reference solution}} \times \frac{\frac{\text{Weight of Std in reference solution}}{25} \times \frac{1}{200} \times 25}{\text{Weight of Sample In test solution}} \times 100$$

The following examples are provided to enable one skilled in the art to practice the invention and are merely illustrative of the invention. The examples should not be read as limiting the scope of the invention as defined in the features and advantages.

EXAMPLES

Example 1

Preparation of N-{2-(benzyloxy)-5-[(2R)-oxiran-2-yl]phenyl}formamide, Compound of Formula IV a) Synthesis of [(1R)-1-[4-(benzyloxy)-3-nitrophenyl]-2-bromoethanol]

Method-I:

To a solution of 10.64 gm (1R,2S)-amino indanol in 0.5 liter tetrahydrofuran under nitrogen was added 13.55 ml of borane-dimethylsulfide complex at about 25-30° C. and maintained for about 30 minutes. Simultaneously a solution of 500 gm of 4-benzyloxy-3-nitro bromoacetophenone in 3.50 liter tetrahydrofuran was prepared. This prepared solution and 101.65 ml of Borane DMS complex was simultaneously added to the reaction mass within about 2-3 hours. The reaction mass was quenched by addition of methanol with control temperature at about 25-30° C. and organic volatiles were distilled out completely under vacuum to yield an oily residue. The oily residue was dissolved in toluene and washed twice with mixture of sulphuric acid and 50% hydrogen peroxide. Further toluene layer was washed with water followed by brine solution and concentrated under vacuum at about 30-35° C. Subsequently 2 liters of toluene:heptane (3:2) mixture was added to the residue and heated to about 60-65° C. for about 15-20 minutes and cooled the reaction mass to about 5-10° C. gradually and maintained for about 1 hour. The precipitated product was filtered and washed the wet product with 0.5 liter toluene:heptane mixture. The product obtained was dried at about 35-40° C. in vacuum oven for about 8 hours to yield 350 gm titled compound.

Method-II:

To the solution of (1R,2S)-amino indanol (21.28 gm) in 7 liters of tetrahydrofuran under nitrogen, Borane-DMS (230 ml) was added at about 25-30° C., and was maintained for about 30 minutes. Further 4-Benzyloxy-3-nitro bromo acetophenone (1 Kg) was added in equal lots to the Borane complex within about 3 hours. After complete addition the reaction mass was maintained at about 25-30° C. for about 30 minutes. The reaction was quenched by addition of methanol. Further the solvent was concentrated completely under vacuum to obtain residue. 5 volume of 0.2 M solution of sulfuric acid and 50% $H_2O_2$ solution were added sequentially when the product precipitated out after about 10-15 minutes. The reaction mass was stirred for about 2 hours at about 25-30° C. The product was filtered and washed with water. The wet product was dried at about 40° C. under vacuum for about 10-12 hours. This crude product was further purified in 4 liter toluene:heptane mixture (3:2) and heated to about 60-65° C. for about 30 minutes and slowly cooled the reaction mass to about 15-20° C. and maintained for about 1 hour. The precipitated product was filtered and washed with 1 liter of toluene:heptane mixture. The product obtained was dried at about 35-40° C. in vacuum oven for about 8 hours to yield 0.80 Kg titled compound. HPLC Purity: >98%; Chiral Purity: >98% b) Synthesis of [(1R)-1-[3-amino-4-(benzyloxy)phenyl]-2-bromoethanol]

To solution of 0.40 kg of [(1R)-1-[4-(benzyloxy)-3-nitrophenyl]-2-bromoethanol] and 4 liter of acetic acid, 0.317 Kg of iron powder was charged at about 25-30° C. Further the reaction mass was stirred at about 25-30° C. for about 5-6 hours. The reaction mass was quenched in 20 liter ice cold water and stirred for about 15-20 minutes. 4 liter of ethyl acetate was charged to the reaction mass and stirred further for about 25-30 minutes. The ethyl acetate layer was separated from the aqueous layer and additionally the aqueous layer was extracted with ethyl acetate twice. The combined ethyl acetate layers were washed with saturated sodium bicarbonate solution followed by water and brine. Finally the organic layer was dried over sodium sulphate and filtered through hyflobed. The ethyl acetate layer was concentrated under vacuum. To the residue obtained 1.2 liter of ethyl acetate was added and temperature was raised to about 50-55° C. to get a clear solution. To this clear solution, 3.6 liter of hexane was added slowly. The reaction mass was cooled to about 25-30° C. and maintained for about 2 hours and the solid obtained was filtered and washed with hexane. The product obtained was dried at about 30-35° C. for about 8 hours under vacuum to yield 0.32 Kg titled compound.

c) Synthesis of [N-{2-(benzyloxy)-5-[(1R)-2-bromo-1-hydroxyethyl]phenyl}formamide]

Method-I:

To a 1 liter four necked flask with nitrogen, 0.304 kg of acetic anhydride was charged. Subsequently 0.274 kg of formic acid was added slowly at about 0-5° C. and the reaction mass was maintained for about 30-45 minutes. Meanwhile in another flask 0.32 kg of (1R)-1-[3-amino-4-(benzyloxy)phenyl]-2-bromoethanol was charged followed by 3.2 liter tetrahydrofuran under nitrogen blanketing. The reaction mass was then cooled to about 0-5° C. Above prepared solution of acetic anhydride/formic acid was added to the above reaction mass at about 0-5° C. within about 20-30 minutes. The reaction mass was stirred and maintained at about 0-5° C. for further 60 minutes. After completion of reaction the solvent was evaporated under vacuum completely at about 35° C. To this residue, 0.64 liter of ethyl acetate was added and distilled the reaction mass to remove the entrapped solvent and the process was repeated. To this residue, 0.64 liter of ethyl acetate: was added, and stirred at about 50-55° C. for about 20-30 minutes followed by addition of 0.96 liter of cyclohexane. The reaction mass was cooled to about 25-30° C. and maintained for about 1 hour. The product was filtered and washed with 0.32 liter of cyclohexane and subsequently dried at about 35-40° C. for about 8 hours under vacuum to yield 0.27 kg of the titled compound.

Method-II:

To the solution of 1 gm (1R)-1-[3-amino-4-(benzyloxy)phenyl]-2-bromoethanol and 0.17 gm of formic acid in 10 ml toluene was added sulfated tungstate (10 wt %) and heated in an oil bath at about 70° C. The reaction mass was cooled to about 25-30° C., followed by addition of toluene under stirring. The insoluble catalyst was filtered on hyflo and washed with toluene. The combined organic layers (both filtrate and washings) were washed with water, dried over anhydrous sodium sulphate and the solvent was evaporated under reduced pressure to get 0.8 gm of the titled compound.

Method-III:

To the solution of 1 gm (1R)-1-[3-amino-4-(benzyloxy)phenyl]-2-bromoethanol and 0.17 g of formic acid in 10 ml tetrahydrofuran was added sulfated tungstate (10 wt %) and heated in an oil bath at about 70° C. and the progress of the reaction was monitored by TLC. The reaction mass was cooled to about 25-30° C., the insoluble catalyst was filtered and washed with tetrahydrofuran. The tetrahydrofuran was evaporated under vacuum and residue was extracted with ethyl acetate. Further this organic layer was washed with water, dried over anhydrous sodium sulphate and the solvent was concentrated under reduced pressure to yield 0.78 gm of the titled compound.

d) Preparation of N-{2-(benzyloxy)-5-[(2R)-oxiran-2-yl]phenyl}formamide, Compound of Formula IV A 20 liter four neck assembly with nitrogen was arranged. 1 kg of N-{2-(benzyloxy)-5-[(1R)-2-bromo-1-hydroxyethyl]phenyl}formamide was charged followed by addition of 5 liter of tetrahydrofuran and 5 liter of methanol to the reaction mass. 0.591 kg of potassium carbonate was added to the reaction mass. The reaction mass was stirred and maintained at about 25-30° C. for about 2 hours. The completion of the reaction was monitored by HPLC. After completion of the reaction the organic volatiles were distilled out completely under vacuum. 10 liter of toluene was charged to the reaction mass and the reaction mass was stirred at about 25-30° C. for further about 1 hour. The reaction mass was filtered through hyflo and the bed washed with toluene. The toluene layer was then concentrated to get the oily residue under vacuum. To this obtained residue 10 liter toluene/n-heptane mixture (1:1) was added and the mixture was refluxed at about 80-110° C. The reaction mass was then cooled slowly to about 25-30° C. and stirred for about 2-3 hours when product precipitated out. The product was filtered and washed with 1 liter mixture of toluene and n-heptane and dried for about 10 hours under vacuum at about 35-40° C. to yield 0.60 kg of titled compound. Purity: >95%; SOR: 5.1° and Melting Point: 79 to 80° C.

Example 2

Preparation of [(2R)—N-benzyl-1-(4-methoxyphenyl)propan-2-amine], Compound of Formula V a) Synthesis of [N-benzyl-1-(4-methoxyphenyl)propan-2-amine Mandalate Salt]

To a clean and dry 10 liter autoclave, 5 liters of methanol and 1 kg of 1-(p-methoxyphenyl)-2-propanone was charged. To this 0.650 kg of benzyl amine was added at about 25-30° C. The temperature of the reaction mass was slowly raised to about 40-45° C. and maintained for about 2 hours. The reaction temperature was then lowered to 25-30° C. and 1 gm of platinum dioxide catalyst was charged to the autoclave and about 6-8 kg hydrogen pressure was applied. The reaction was maintained at about 6-8 kg hydrogen pressure for about 3-4 hours. The progress of the reaction was monitored by HPLC. After completion of reaction, the reaction mass was filtered through hyflo bed and subsequently washed with methanol. The filtrate was collected and transferred to another 10 liter RBF. 0.950 kg L-(+)-mandelic acid was added to the reaction mass under stirring. The reaction temperature was then raised to about 70-75° C. and maintained for about 30-45 minutes. The reaction mass was slowly cooled to about 25-30° C. to precipitate out the product. The product obtained was filtered, washed with methanol and dried at about 45-50° C. for about 6-8 hours to yield 1.4 kg of the titled compound.

Purification:

To a 5 liter four neck assembly, 1 Kg of N-benzyl-1-(4-methoxyphenyl)propan-2-amine mandalate salt was charged followed by 3 liters of methanol at about 25-30° C. The reaction temperature was raised to reflux. The reaction mass was maintained at about 65-70° C., for about 25-30 minutes and then slowly cooled to about 25-30° C. and maintained for about 1 hour with stirring. The product was filtered, washed with methanol. The wet cake was dried for about 1 hour at about 45-50° C. for about 6-8 hours. Purification can be repeated to achieve the desired chiral purity. Chiral Purity>98%; Chemical Purity: >99%.

b) Synthesis of [(2R)—N-benzyl-1-(4-methoxyphenyl)propan-2-amine]

To a 10 liter four neck assembly 10 liter of water and 1 kg of N-benzyl-1-(4-methoxyphenyl)propan-2-amine mandalate salt was charged followed by 8 liter of methylene dichloride. To this 0.8 liter of 20% sodium hydroxide solution was slowly charged at about 25-30° C. to adjust pH>12. The reaction mass was maintained for next 2 hours. The organic layer was separated from aqueous layer and the aqueous layer was extracted with methylene dichloride. The total organic layer was combined and washed with water followed by washing with brine solution. Methylene dichloride layer was charged to the flask and subsequently 1.5 kg Neutral alumina was added and stirred for about 2 hours. The methylene dichloride layer was filtered to remove neutral alumina and concentrated completely under vacuum to yield 0.6 kg of title compound. Chiral Purity: >98%; Chemical Purity: >98%.

Example 3

Preparation of Compound of Formula III

A 2 liter assembly was arranged and 80.9 gm of N-{2-(benzyloxy)-5[(2R)-oxiran-2-yl]phenyl}formamide (compound of formula IV) and 72.8 gm of (2R)—N-benzyl-1-(4-methoxyphenyl)propan-2-amine (compound of formula V) were added sequentially. The temperature of the reaction mass was slowly raised to about 90-110° C. and maintained at that temperature for about 12 hours with stirring. Subsequently the reaction mass was cooled to about 25-30° C. to obtain compound of Formula III.

Example 4

Preparation of arformoterol D-(−)-tartrate Compound of Formula II

Method-I:

To a clean and dry 2 liter Autoclave, 100 gm of compound of formula III was charged followed by addition of 750 ml isopropyl alcohol and 5 gm of 10% Pd/C. 3-3.5 kg of hydrogen pressure was applied to the reaction mass and the reaction mass was maintained at about 35-36° C. and 3.5 kg pressure for about 10-12 hours. The progress of the reaction was monitored by HPLC. After the completion of reaction, the mass was filtered through hyflobed and the bed was washed with 50 ml isopropyl alcohol. The total filtrate was combined and charged to a 2 liter four necked flask followed by addition of 200 ml of toluene under nitrogen. To this reaction mass D-(−)-tartaric acid solution was added slowly (Prepared by using 34.3 gm D-(−)-tartaric acid in 100 ml water) at about 25-30° C. Subsequently the reaction mass was stirred and maintained at about 25-30° C. for about 3 hours. The salt precipitated out was filtered and washed with isopropyl alcohol and dried at about 40-45° C. under vacuum for about 6-8 hours to yield 70 gm titled compound. Chemical Purity: >90%, Method-II:

To a clean and dry 2 liter Autoclave, 100 gm of compound of formula III was taken in 1050 ml ethanol:isopropyl alcohol mixture (7:3 ratio) and 7.5 gm of 10% Pd on C (50% wet). 4-4.5 kg of hydrogen pressure was slowly applied to the reaction mass. The temperature was raised to about 50-55° C. and maintained for about 3-4 hours. The reaction mass was filtered through hyflo bed and washed with 50 ml isopropyl alcohol. The filtrate was combined and charged to a flask followed by addition of D-(−)-tartaric acid solution. (Prepared by using 34.3 gm D-(−)-tartaric acid in 100 ml water) at about 25-30° C. The reaction mass was stirred and maintained for about 25-30° C. for about 3 hours. The product obtained was filtered and washed with isopropyl alcohol and dried at about 40-45° C. under vacuum for about 6-8 hours to yield 70 gm titled compound. Chemical Purity: >90%.

Purification:

To a clean 2 liter, 4-neck flask 525 ml of tetrahydrofuran was charged followed by addition of 65 gm of the crude compound of formula IIa at about 25-30° C. The reaction temperature was slowly raised to reflux at about 65-70° C. and DM water was added slowly till clear solution was observed. The homogenous reaction mass was stirred for about 15-20 minutes and then 790 ml of tetrahydrofuran was slowly added to the reaction mass. The reaction mass was then allowed to cool naturally and stirring continued for further about 5-6 hours at about 25-30° C. The product precipitated out was filtered and washed with tetrahydrofuran. The wet product was then dried at about 30-35° C. under vacuum for about 6-8 hours. The same purification procedure was repeated two more times till required purity was achieved. Chemical Purity: >99.5%

Data of Pure arformoterol D-(−)-tartrate

Chemical purity: 99.76%; Formula A=0.15%; Formula B=0.02%; Chiral purity: 99.76%; SOR=−44° (C=0.61% in water); Melting point: 186.10° C. by DSC; IR: 3489, 3445, 3370, 3003, 2987, 2958, 2889, 2837, 2754, 1735, 1677.

| XRD Table of arformoterol D-(−)-tartrate | | |
|---|---|---|
| Peak Number | °2Th. | Intensity |
| 1 | 3.82 | 19.47 |
| 2 | 15.44 | 100 |
| 3 | 17.79 | 11.97 |
| 4 | 18.13 | 4.57 |
| 5 | 19.28 | 7.53 |
| 6 | 22.83 | 9.69 |
| 7 | 23.91 | 6.20 |
| 8 | 24.41 | 5.87 |
| 9 | 25.52 | 10.34 |
| 10 | 27.07 | 5.31 |
| 11 | 30.98 | 4.99 |
| 12 | 34.99 | 7.35 |
| 13 | 36.25 | 4.52 |
| 14 | 38.98 | 9.53 |

Example 5

Preparation of arformoterol L-(+)-tartrate, Compound of Formula Ia

To a clean 5 L, 4-neck flask 2 L, DM water was charged followed by addition of 100 gm of arformoterol D-(−)-tartrate at 25-30° C. Subsequently 1 L of ethyl acetate was charged to the solution followed by slow addition of 85 gm of sodium bicarbonate. 200 gm of sodium chloride was added to the reaction mass and the reaction mass was stirred for about 30 minutes and two layers were separated. The aqueous layer was then extracted twice with 500 ml ethyl acetate. The combined organic layer was then dried over sodium sulphate. The organic layer was distilled off completely under vacuum followed by codistillation twice of 300 ml isopropanol each. The residue was then degassed for about one hour and dissolved in 800 ml of isopropanol and followed by addition of 200 ml of toluene. In 2 L flask subsequently Aq. L-(+)-Tartaric acid solution (36.43 gm of L-(+)-tartaric acid dissolved in 100 ml of DM water) was added slowly to the reaction mass under stirring. After complete addition, the stirring was continued for 3 hours at about 25-30° C. The precipitated product was filtered and the wet cake was washed with 200 ml isopropyl alcohol and dried at about 40-45° C. under vacuum for about 6-8 hours. Further dried product was micronized to yield 65 gm of Arformoterol L(+)tartrate.

Data of arformoterol L-(+)-Tartrate

Chemical purity: 99.65% Formula A=0.09%; Formula B=below detection limit; Chiral purity: 100%; SOR=−28.6° (C=0.61% in water); Melting point: 178.54° C. by DSC; IR: 3840, 3736, 3459, 3398, 3317, 3103, 2985, 2938, 2843, 2738, 2536, 1660.

| XRD Table of arformoterol L-(+)-Tartrate | | |
|---|---|---|
| Peak Number | 2-Theta | Intensity |
| 1 | 4.32 | 11.77 |
| 2 | 8.69 | 100 |
| 3 | 12.26 | 18.44 |
| 4 | 13.85 | 18.79 |
| 5 | 16.45 | 14.41 |
| 6 | 17.44 | 94.36 |
| 7 | 19.38 | 30.40 |
| 8 | 20.63 | 74.72 |
| 9 | 21.96 | 46.88 |
| 10 | 22.74 | 44.62 |
| 11 | 25.29 | 19.05 |
| 12 | 25.65 | 17.05 |
| 13 | 26.05 | 15.63 |
| 14 | 26.29 | 22.21 |
| 15 | 26.62 | 13.55 |
| 16 | 28.57 | 12.54 |

Example 6

Preparation of arformoterol L(+) Tartrate, Compound of Formula Ia

Method I:

To a clean and dry 2 L Autoclave, 100 gm of compound of formula III was added, followed by addition of 750 ml isopropyl alcohol and 7.5 gm 10% Pd on C. 3-3.5 kg hydrogen pressure was applied to the reaction mass and the reaction mass was maintained at about 35-36° C. and 3.5 kg pressure for about 10-12 hours. The reaction mass was filtered through hyflo and washed with 50 ml isopropyl alcohol. The filtrate was collected and charged to a 2 L flask followed by addition of 200 ml of toluene under nitrogen blanketing. To this reaction mass L-(+)-tartaric acid solution prepared by using 34.3 gm of L-(+)-Tartaric acid in 100 ml water was added at about 25-30° C. The reaction mass was stirred and maintained for about 25-30° C. for about 3 hours. The reaction mass was filtered and the wet cake was washed with 100 ml isopropyl alcohol. The wet cake was suck dried for about one hour. The crude material was dried at about 35-40° C. under vacuum for about 6-8 hours to yield 68 gm titled compound. Chemical Purity: 97.33%

Method II:

To a clean and dry 2 L Autoclave, 100 gm of compound of formula III was added, followed by addition of 750 ml isopropyl alcohol and 7.5 gm 10% Pd on C. 3-3.5 kg hydrogen pressure was applied to the reaction mass and the reaction mass maintained at about 35-36° C. and 3.5 Kg pressure for about 10-12 hours. The reaction mass was filtered through hyflo and washed with 50 ml isopropyl alcohol. The total filtrates were combined and the organic volatiles were removed under reduced pressure. To this residue was added 900 ml of tetrahydrofuran followed by slow addition of L-(+)-tartaric acid solution (34.3 gm of L-(+)-tartaric acid in 30 ml water) at about 25-30° C. The reaction mass was stirred and maintained for about 25-30° C. for about 3 hours. The reaction mass was filtered and the wet cake was washed with 100 ml tetrahydrofuran. The crude material was dried at about 35-40° C. under vacuum for about 6-8 hours to yield 60 gm of titled compound.

Purification:

To a clean 2 liter 4-neck flask 520 ml of tetrahydrofuran was charged followed by addition of 65 gm of the crude arformoterol L-(+)-Tartrate at about 25-30° C. The reaction temperature was raised to reflux at about 65-70° C. and DM water was added slowly till clear solution was observed. The reaction mass was stirred for about 15-20 minutes under hot condition and then 780 ml of tetrahydrofuran was added to the reaction mass. The reaction mass was then allowed to cool and stirring continued for about 5-6 hours at about 25-30° C. The precipitated salt was filtered, washed with tetrahydrofuran and dried at about 30-35° C. under vacuum for about 6-8 hours. Same purification process can be repeated to achieve the desired chemical and chiral purity.

Data of Pure L-(+)-Tartrate:

Chemical purity: 99.88%; Chiral purity: 100%; SOR=−29.2° (C=0.61% in water) DSC: Endotherm at 128.4° C., 174.82° C., 180.26° C. and exotherm at 137.21° C. IR: 3854, 3490, 3358, 3076, 2976, 1660, 1597

XRD of arformoterol L-(+)-tartrate

| Peak Number | 2-Theta | Intensity |
|---|---|---|
| 1 | 6.63 | 90.57 |
| 2 | 7.64 | 12.09 |
| 3 | 9.26 | 16.12 |
| 4 | 10.81 | 10.92 |
| 5 | 11.44 | 12.18 |
| 6 | 12.65 | 33.07 |
| 7 | 13.22 | 29.12 |
| 8 | 13.83 | 12.85 |
| 9 | 14.36 | 12.43 |
| 10 | 15.30 | 11.95 |
| 11 | 16.20 | 41.20 |
| 12 | 16.67 | 19.06 |
| 13 | 17.25 | 32.02 |
| 14 | 17.92 | 42.91 |
| 15 | 18.74 | 100 |
| 16 | 19.86 | 80.62 |
| 17 | 20.28 | 42.54 |
| 18 | 21.77 | 45.16 |
| 19 | 22.97 | 85.40 |
| 20 | 23.64 | 75.78 |
| 21 | 24.44 | 38.19 |
| 22 | 25.08 | 24.53 |
| 23 | 26.56 | 25.60 |
| 24 | 34.86 | 10.68 |
| 25 | 36.30 | 11.22 |

Comparative Example

Preparation of arformoterol L-(+)-tartrate, Compound of Formula Ia

To a clean and dry 2 L Autoclave, 30 gm of compound of formula III was added, followed by addition of 248 ml isopropyl alcohol, 62 ml toluene and 10% Pd on C with 3-4 kg hydrogen pressure. The reaction mass was filtered through hyflo bed and aqueous L-tartaric acid solution (9.32 gm of L-tartaric acid dissolved in 46.5 ml of water) was added to reaction mass and maintained for 1-2 hour. The reaction mass was cooled to 10-15° C. and further maintained for 2 hours. The precipitated arformoterol L-(+)-tartrate was filtered and washed with about 50 ml of IPA-Toluene mix (8:2) and dried under vacuum at 35-40° C. to form 21 gm of arformoterol L(+) tartrate. Chemical Purity: 95.88% by HPLC.

| Impurity | Area percentage |
|---|---|
| Formula A | 3.49% |
| Formula B | 0.04% |
| Formula D | 0.05% |
| Formula E | 0.22% |

The invention claimed is:

1. A process for the preparation of arformoterol L-(+)-tartrate, a compound of Formula Ia,

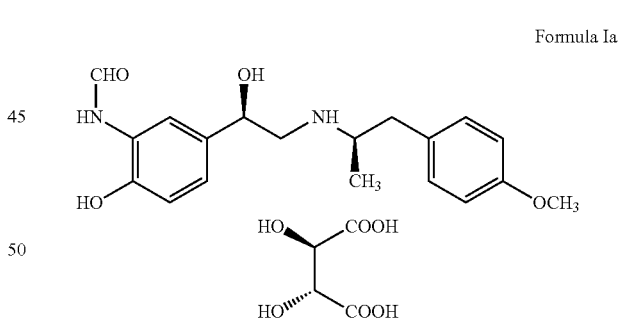

Formula Ia wherein the level of compounds of formula A or B, is less than 0.15% w/w relative to the amount of arformoterol L-(+)-tartrate as determined by HPLC,

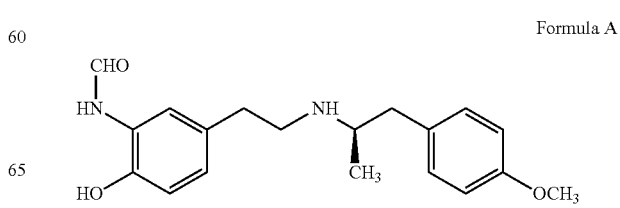

Formula A

-continued

Formula B

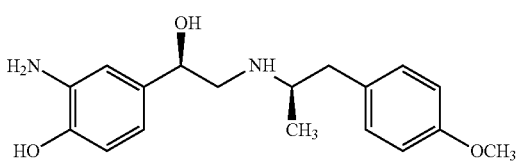

composing: a) reacting crude arformoterol, a compound of Formula I

Formula I

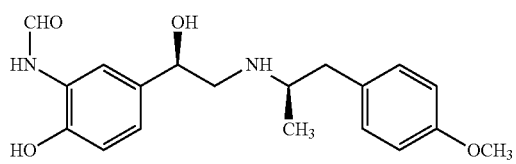

with D-(+)-tartaric acid to form arformoterol D-(−)-tartrate, a compound of formula II; and Formula II

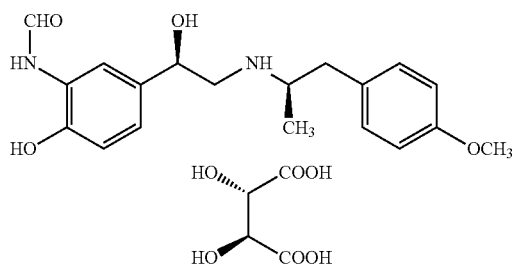

b) reacting the arformoterol D-(−)-tartrate, the compound of formula II, with a base and L-(+)-tartaric acid, to form arformoterol L-(+)-tartrate, a compound of Formula Ia.

2. The process of claim 1, wherein arformoterol D-(−)-tartrate, a compound of formula II, is subjected to purification.

3. The process of claim 2, wherein arformoterol D-(−)-tartrate, a compound of formula II, is subjected to purification by crystallization in a solvent system.

4. The process of claim 3, wherein the solvent system comprises ether and water.

5. The process of claim 1, wherein arformoterol D-(−)-tartrate, a compound of formula II has a chemical purity of at least 95% as determined by HPLC.

6. The process of claim 1, wherein in step b) the arformoterol D-(−)-tartrate, the compound of formula II, is reacted with a base to obtain arformoterol, followed by reacting the arformoterol with L-(+)-tartaric acid in a mixture of toluene and isopropanol to form arformoterol L-(+)-tartrate.

7. The process of claim 6, wherein the isopropanol and toluene are used in the ratio of 8:2 v/v.

8. The process of claim 6, wherein an aqueous solution of L-(+)-tartaric acid is used.

9. The process of claim 8, wherein the aqueous solution of L-(+)-tartaric acid is used in a proportion such that isopropanol:toluene:water is in the ratio of 8:2:1 v/v, for 1 part by weight of arformoterol D-(−)-tartrate.

10. The process of claim 9, wherein the arformoterol L-(+)-tartrate, to compound of Formula Ia, is isolated in crystalline polymorphic Form B.

11. The process of claim 1, wherein arformoterol D-(−)-tartrate, the compound of formula II, is thereafter convened to arformoterol L-(+)-tartrate, a compound of Formula Ia.

* * * * *